United States Patent [19]

Dotter

[11] Patent Number: 4,503,569
[45] Date of Patent: Mar. 12, 1985

[54] TRANSLUMINALLY PLACED EXPANDABLE GRAFT PROSTHESIS

[76] Inventor: Charles T. Dotter, 4004 SW. Greenleaf Dr., Portland, Oreg. 97221

[21] Appl. No.: 471,856

[22] Filed: Mar. 3, 1983

[51] Int. Cl.[3] .......................... A61F 1/00; A61F 1/24; A61B 17/00
[52] U.S. Cl. .................................................. 3/1.4; 3/1; 128/303 R; 128/334 R; 128/343; 128/325; 604/8
[58] Field of Search .................. 3/1, 1 A, 1.4; 128/334 R, 325, 303 R, 303.1, 303.11, 303.12, 343; 604/8

[56] References Cited

U.S. PATENT DOCUMENTS

| 3,657,744 | 4/1972 | Ersek | 3/1 A |
|---|---|---|---|
| 3,713,175 | 1/1973 | Weisman | 3/1.4 X |
| 3,827,426 | 8/1974 | Page et al. | 3/1 |
| 3,889,685 | 6/1975 | Miller et al. | 604/8 |
| 3,993,078 | 11/1976 | Bergentz et al. | 3/1.4 X |
| 4,130,904 | 12/1978 | Whalen | 3/1.4 |
| 4,140,126 | 2/1979 | Choudhury | 3/1.4 X |
| 4,183,102 | 1/1980 | Guiset | 3/1.4 |
| 4,299,226 | 11/1981 | Banka | 128/325 X |
| 4,300,244 | 11/1981 | Bokros | 3/1.4 |
| 4,315,509 | 2/1982 | Smit | 128/303 R |

FOREIGN PATENT DOCUMENTS 260819  10/1970  U.S.S.R. ................. 3/1 A

Primary Examiner—Ronald L. Frinks
Attorney, Agent, or Firm—Woodard, Weikart, Emhardt & Naughton

[57] ABSTRACT

A transluminally placed endovascular graft prosthesis includes a helically wound coil having a generally tubular shape and is made of a shape memory Nitinol alloy having a transition temperature in the range of 115°–125° F. After placement within a body blood vessel and upon heating of the prosthesis to its transition temperature, the prosthesis expands so as to become firmly anchored to the inside wall of the body blood vessel. After expansion the diameter of the lumen of the prosthesis is approximately equal to the diameter of the body blood vessel passageway. The prosthesis may also be used in other body passageways.

14 Claims, 7 Drawing Figures

TRANSLUMINALLY PLACED EXPANDABLE GRAFT PROSTHESIS

BACKGROUND OF THE INVENTION

1. Field of the Invention

The present invention relates generally to the field of prosthetic devices for use within a body passageway or duct and, more particularly, to the area of transluminally placed endovascular grafts prosthesis which are particularly useful for repairing blood vessels narrowed or occluded by disease.

2. Description of the Prior Art

Transluminal endovascular grafting has been demonstrated by experimentation to present a possible alternative to conventional vascular surgery. Transluminal endovascular grafting involves the percutaneous insertion into a blood vessel of a tubular prosthetic graft and its transluminal catheter placement at the desired location within the vascular system. Advantages of this method over conventional vascular surgery include obviating the need for surgically exposing, incising, removing, replacing or bypassing the defective blood vessel.

Despite the major advantages afforded by transluminal endovascular graft placement, this method inherently presents certain problems. During placement the graft prosthesis must be smaller than the lumen of the blood vessel through which it is moved by a catheter into the desired location. Since the lumen of the initially narrowed segment of blood vessel should, after graft placement, be approximately equal to that of the adjacent undamaged portions, it is necessry that the graft be increased in diameter after placement.

Another problem concerns the possible migration of the graft after placement at a desired location. Thus, the graft must be provided means for permanently anchoring in place.

Through previous experimentation, I have shown that the use of an expandable tubular coilspring prosthesis provides means for controlling the size of the prosthesis to facilitate placement and anchoring. The use of such a prosthesis was described in my following publication: Dotter, C. T.: *Transluminally-placed Coilspring Endarterial Tube Grafts*, Investigative Radiology, Vol. 4, No. 5, Sept.-Oct., 1969. As disclosed in this publication, the coilspring endovascular prosthesis can be either stretched out or wound up and hooked to a controlling mandrel so as to reduce the diameter of the prosthesis for easier introduction and placement. After placement and upon externally-effected release from the mandrel, the coilspring prosthesis automatically expands to provide a larger lumen and better anchoring at the site of placement.

The use of spring force to expand the diameter of a coilspring prosthesis after vascular placement presents a disadvantage to the degree that is unnecessarily complicates the grafting procedure, requiring increased skill of the physician in effecting implantation and also requiring a fairly complicated mechanism to effect external release from the mandrel. Thus, it would be desirable to employ a simpler method for externally controlling the diameter of the prosthesis within the body.

One type of graft prosthesis which is expandable within a blood vessel is disclosed in U.S. Pat. No. 4,140,126 to Choudhury. This refers to an elongated tube having a plurality of longitudinal folds interspaced with a plurality of radially spaced anchoring pins and mounted upon upper and lower expansion rings. The elongated tube is mechanically expanded by release of the upper and lower expansion rings. This device is characterized by a relatively complicated mechanical means for expanding the prosthesis within the blood vessel and is not adaptable for use as a prosthetic graft to repair an occluded segment of a blood vessel.

U.S. Pat. No. 4,130,904 to Whalen discloses a prosthetic blood conduit which includes a helically formed coil. The device is otherwise different than the present invention and is not adapted for implantation within an occluded blood vessel.

U.S. Pat. No. 3,713,175 to Weisman discloses a cobalt-chromium-tungsten-nickel-molybdenum alloy cardiovascular implant device. The allow is not disclosed to have shape memory properties and the implant is not temperature expandable for implantation purposes.

U.S. Pat. No. 4,159,719 to Haerr and U.S. Pat. No. 4,183,102 to Guiset both disclose devices which are expandable within a body duct, but are otherwise different from the present invention.

Accordingly, it is an object of the present invention to provide an improved graft prosthesis for therapeutic use within a body passageway or duct.

It is a further object of this invention to provide a prosthetic graft which is temperature expandable for opening or repairing body passageways or ducts, but which is inert to normal body temperature fluctuations.

These and other objects and advantages of the present invention will be apparent from the following description.

SUMMARY OF THE INVENTION

One embodiment of the present invention is characterized by a graft prosthesis which is useful for placement within a body passageway. The prosthesis is an open-ended tube which is expandable from a first configuration sized for transluminal placement within the body passageway to a second configuration having an outer diameter which is larger than the body passageway. The device is formed of a shape memory alloy with a transistion temperature at or above normal body temperature but within bodily tolerance. After placement and upon heating to the approximate transition temperature the graft expands radially so as to expand the diameter of the lumen and become firmly anchored in the body passageway.

DESCRIPTION OF THE PREFERRED EMBODIMENT

Figure 1:
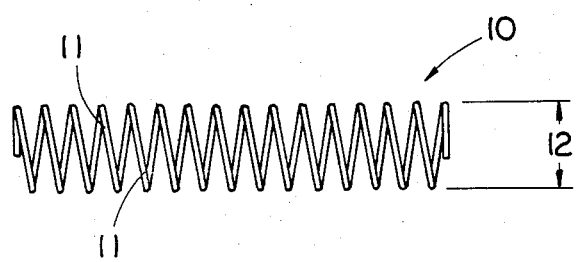
FIGS. 1 and 2 are enlarged elevation views of the expandable graft prosthesis of the present invention in its initial and expanded configuration, respectively.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings, FIG. 1 shows the temperature expandable graft prosthesis of the present invention generally designated as 10. Prothesis 10 is a generally tubular shaped coil of wire having a number of helical turns 11. Prosthesis 10 is made from a shape memory Nitinol alloy with a transition temperature in the range of 115–125 degrees Fahrenheit. Those skilled in the art will appreciate that the transition temperature of the Nitinol family of alloys can be manipulated over a wide range by altering the nickel-titanium ratio, by adding small amounts of other elements, and by varying deformation and annealing processes, therefore, no further description of the composition of the shape memory Nitinol alloy is necessary.

Figure 2:
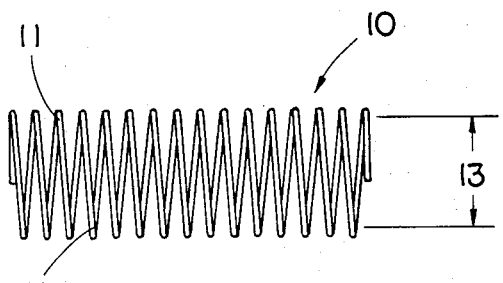

It is to be appreciated that FIG. 1 shows prosthesis 10 in a configuration which renders it suitable for transluminal insertion within a blood vessel or other body passageway. Thus, in the configuration shown in FIG. 1, prothesis 10 has an outer diameter 12 which is less than the corresponding diameter of the blood vessel lumen. FIG. 2 shows prosthesis 10 in the large diameter configuration it would be caused to assume after placement within a narrowed segment of a blood vessel lumen. In this expanded configuration, prosthesis 10 has an inner diameter 13 which is approximately equal to that of the adjacent relatively normal portions of the blood vessel. In the expanded configuration, prosthesis 10 is longitudinally contracted relative to its FIG. 1 configuration.

In order to form the prosthesis 10 so that it will assume the position shown in FIG. 2 when heated to its transition temperature, a length of Nitinol alloy wire is coiled around a mandrel at room temperature so that it has the large diameter configuration shown in FIG. 2. In a manner well known in the art, the wire is then heated until its crystal structure assumes its high-temperature austenite configuration also known as the beta or parent phase. Next, the wire is cooled so that the atoms in the metal rearrange themselves into a crystal structure known as martensite. The coil wire may now be bent and extended into the relatively smaller diameter configuration shown in FIG. 1. Because the coil wire is formed of a Nitinol alloy material, it will revert to the large diameter configuration shown in FIG. 2 when the prosthesis 10 is later heated to a temperature at which the crystal structure reverts to the parent phase. Prosthesis 10 will retain this shape unless it is cooled below a temperature at which martensite transformation of the Nitinol alloy occurs. Since this transformation only begins at temperatures well below normal body temperature, prosthesis 10 cannot return to the unexpanded configuration shown in FIG. 1. The open coil spring configuration shown in FIG. 2 permits prompt firboblastic envelopment and the rapid formation of a new, firmly anchored, autogenous lining surface, thereby favoring continued patency of prosthesis 10 within a body blood vessel. While a helical coil construction is favored for this reason, it should be understood that other constructions may also be employed without departing from the spirit and scope of the invention.

Figure 3:
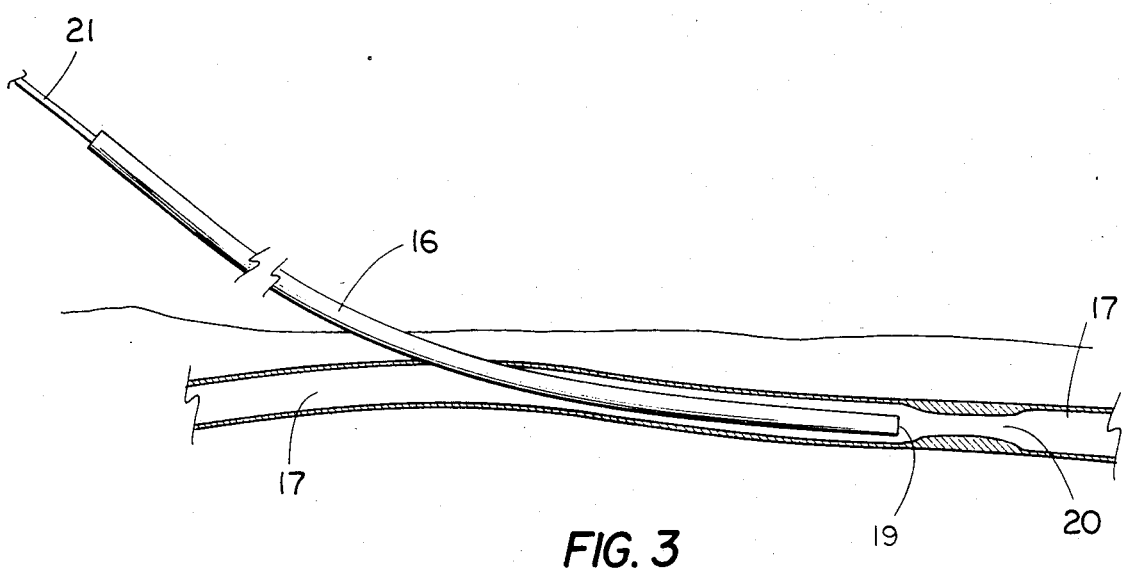
FIGS. 3-6 are enlarged fragmentary cross-sectional views showing successive steps in the implantation of the temperature expandable graft prosthesis of the present invention within a narrowed segment of a body blood vessel.
Figure 4:
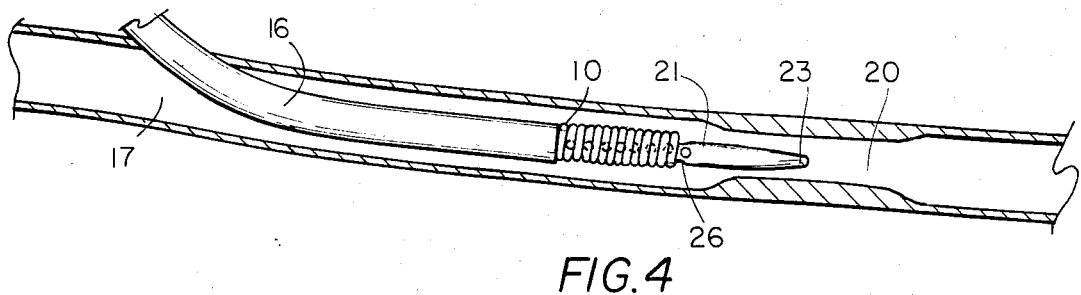
Figure 5:
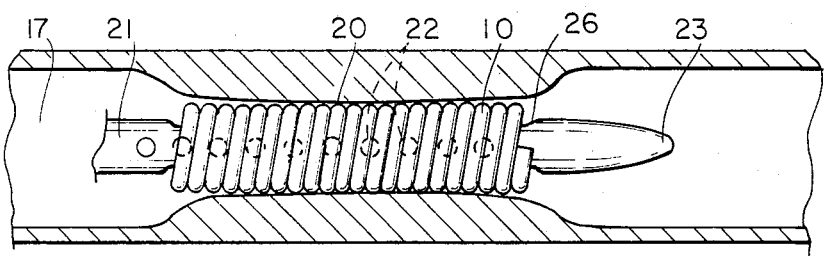

Referring now to FIGS. 3–6, successive steps in the percutaneous transluminal placement of prosthesis 10 within a partially occluded segment of a blood vessel passageway are depicted. As seen in FIG. 3, a conventional catheter 16 is percutaneously inserted into blood vessel lumen 17. This step may be accomplished by normal catheterization techniques. Distal end 19 of catheter 16 is then moved into a position near the narrowed segment 20 of blood vessel lumen 17. As shown in FIGS. 4 and 5, prosthesis 10 in its unexpanded configuration corresponding to that seen in FIG. 1 is pushed over the end of inner guide catheter 21 into a recessed segment 26 at the end of inner guide catheter 21 where it is securely held while being passed by external manipulation of guide catheter 21 through and beyond catheter 16 to the desired site of placement in the narrowed segment 20 of blood vessel lumen 17.

In order to expand prosthesis 10 within narrowed segment 20 of blood vessel lumen 17, it is necessary to heat prosthesis 10 to a temperature at which the Nitinol alloy composing prosthesis 10 reaches its transition temperature and austenite transformation occurs (115–125 degrees Fahrenheit). This is accomplished by injecting a hot fluid through the lumen of guide catheter 21 so as to bathe and trigger expansion of prosthesis 10. It has been determined that a saline solution having a temperature in the range of 130–135 degrees Fahrenheit is acceptable for this purpose. Guide catheter 21 has a series of side apertures 22 positioned along the portion of its length that accommodates prosthesis 10. Apertures 22 serve as the exit points for the injected saline solution, and the tip 23 of guide catheter 21 is closed so that fluid only exits through the side apertures.

Figure 6:
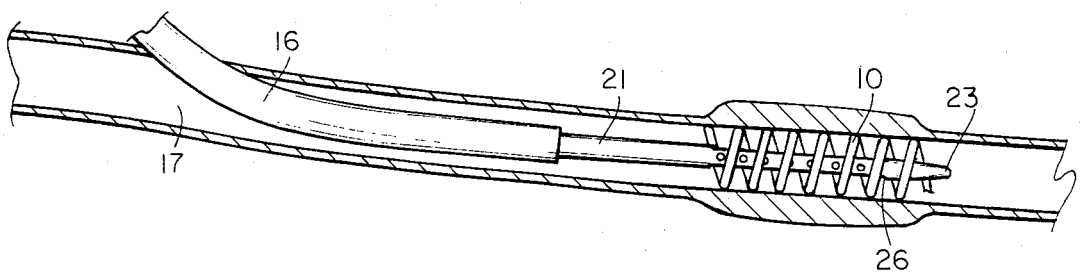
Figure 6A:
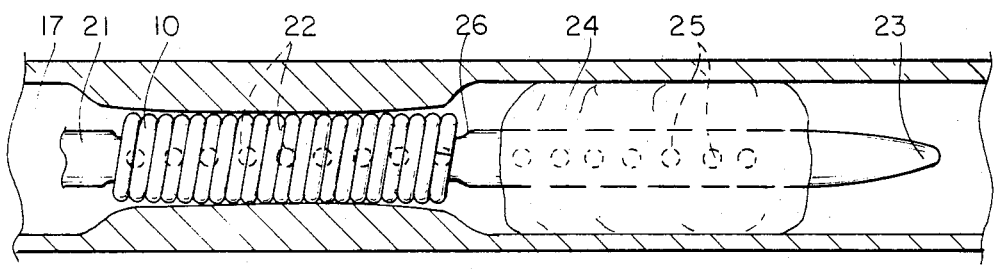
FIG. 6A is an enlarged fragmentary cross-sectional view showing an alternative preferred embodiment of the guide catheter of the present invention having a catheter balloon thereon to prevent too quick wash away or thermodilution of the hot saline solution used to trigger expansion of the graft prosthesis of the present invention.

In applications involving the repair of narrowed blood vessel segments it should also be mentioned that means may be taken to prevent too quick wash away or thermodilution of the hot saline. Such means could be as simple as applying pressure over the blood vessel and above or below graft, thereby stopping blood flow through the vessel during graft expansion. FIG. 6A depicts the use of guide catheter 21 modified to include a catheter ballon 24 thereon which is positioned immediately downstream of prosthesis 10 on guide catheter 21. An additional series of apertures 25 are provided in guide catheter 21 for fluid communication into balloon 24. Triggering of prosthesis 10 by hot saline injected through guide catheter 21 will therefore expand balloon 24 and stop any flow through the blood vessel while at the same time bathing prosthesis 10 with hot saline to trigger its expansion. It is to be understood that while balloon 24 is shown in the distended position it would assume upon injection of the hot saline, balloon 24 would be in a collapsed position during insertion of guide catheter 21 within the blood vessel. Alternatively, balloon 24 could be positioned on the upstream side of prosthesis 10 or even both sides if such becomes desirable for any reason.

As the Nitinol alloy in prosthesis 10 reaches its transition temperature (125–130 degrees Fahrenheit) it promptly reassumes the large diameter configuration shown in FIG. 2. Once this expanded configuration is attained as seen in FIG. 6, it becomes possible to withdraw guide catheter 21, thereby leaving prosthesis 10 securely locked by outward pressure against the blood vessel wall.

It is to be understood that other means and methods for placing prosthesis 10 within a narrowed blood vessel segment may occur to persons normally skilled in the art and the invention is not restricted to the catheter introduction and placement system described herein. For instance, by the choice of an appropriately characterized Nitinol or other shape-memory alloy, artificially elevated or normal body temperature can be used to cause a desired change in configuration of a percutaneously placed body prosthesis. In order to use normal body temperature, a straight length of Nitinol or other type of prestressed shape-memory alloy wire having a transistion temperature of 98.6° F. can be inserted at room temperature through a small catheter and on exit therefrom, thermally caused by body temperature to assume a desired initially imparted coil or other configuration with the body.

In addition to producing expansion of prosthesis 10 by injection of a hot saline solution or exposure to normal body temperature of a prosthesis having a transition temperature equal to normal body temperature, expansion thereof may also be produced by induction or microwave warming of the prosthesis through the skin, or by passing a current through the graft prosthesis from electrodes located on the guide catheter or by a separate heating device temporarily positioned through a catheter.

Further, while prosthesis 10 has been described for use in expanding partially occluded segments of a blood vessel passageway, it is to be understood that with only minor modifications thereto prosthesis 10 may be used for many purposes such as the following: (1) stent supportive graft placement within blocked arteries opened by transluminal catheter recanalization but likely to collapse in the absence of an internal support; (2) similar use following catheter passage through mediastinal and other veins occluded by inoperable cancers; (3) reinforcement of catheter created intrahepatic communications between portal and hepatic veins in patients suffering from portal hypertension; (4) coil spring stenting of narrowing of the esophagas, the intestine, the ureters, and the urethra; (5) stent-reinforcement of reopened and previously obstructed bile ducts; and (6) biliary cirrhosis.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A transluminally-placed endovascular graft prosthesis, comprising:
   a tubular shaped member having first and second open ends and lumen therethrough, said member sized for transluminal placement within a body blood vessel, said member made of a shape memory material having a transition temperature in a range at or above normal body temperature such that after placement within said body blood vessel and upon heating of said member to a temperature higher than normal body temperature said member expands radially so as to become firmly anchored to the inside wall of said body blood vessel, expansion of said member also expanding the diameter of said lumen.

2. The apparatus of claim 1, wherein said tubular shaped member is a helically wound coil spring.

3. The apparatus of claim 1, wherein said shape memory material is a Nitinol alloy.

4. The apparatus of claim 3, wherein said Nitinol alloy has a transition temperature in a range between 115–125 degrees Fahrenheit.

5. The apparatus of claim 1, wherein the diameter of said lumen in its expanded position is approximately equal to the diameter of the passageway of said body blood vessel.

6. The apparatus of claim 1, wherein said transition temperature is in the range of 115–125 degrees Fahrenheit.

7. A graft prosthesis for placement within a body passageway comprising:
   an elongate member having first and second open ends and a lumen therethrough, said member expandable from a first position wherein said member is sized for transluminal placement within said body passageway to a second position wherein said member is larger than said body passageway, said member expanding in response to an increase in temperature such that after placement within said body passageway and upon heating of said member to a temperature equal to or in excess of normal body temperature said member expands radially so as to become firmly anchored in said body passageway, expansion of said member also causing expansion of the diameter of said lumen.

8. The apparatus of claim 7, wherein said member is formed of a shape memory Nitinol alloy.

9. The apparatus of claim 8, wherein the transition temperature of said Nitinol alloy is in a range between 115–125 degrees Fahrenheit.

10. A method for expanding a narrowed segment of a body blood vessel passageway comprising the steps of:
    (1) inserting a vascular prosthesis within a narrowed segment of a blood vessel passageway; and
    (2) expanding said prosthesis within said narrowed segment of said blood vessel passageway by increasing the temperature of said prosthesis to a level which is in a range at or above normal body temperature thereby expanding the lumen of said prosthesis and also the blood vessel passageway along said narrowed segment.

11. The method of claim 10 wherein step (1) is accomplished by transluminally inserting said vascular prosthesis by catherization of said body blood vessel.

12. The method of claim 11 wherein step (2) is accomplished by injecting a hot fluid within said body blood vessel so as to bathe said prosthesis and thereby trigger its expansion.

13. The method of claim 12 wherein injection of said hot fluid also expands a catheter balloon thereby limiting fluid flow through said body blood vessel and decreasing thermodilution of said hot fluid within said vessel.

14. A method for implanting a prosthesis within a body passageway comprising the steps of:
    (1) inserting said prosthesis within said body passageway by catherization of said passageway; and
    (2) expanding said prosthesis at a desired location within said body passageway by increasing the temperature of said prosthesis to a level which is in a range at or above normal body temperature thereby expanding the lumen of said prosthesis within said body passageway.

* * * * *

UNITED STATES PATENT AND TRADEMARK OFFICE
CERTIFICATE OF CORRECTION

PATENT NO. : 4,503,569
DATED : March 12, 1985
INVENTOR(S) : Charles T. Dotter

It is certified that error appears in the above-identified patent and that said Letters Patent is hereby corrected as shown below:

Column 2, line 16, change "allow" to -- alloy --.

Signed and Sealed this

Twenty-seventh Day of August 1985

[SEAL]

Attest:

DONALD J. QUIGG

Attesting Officer     Acting Commissioner of Patents and Trademarks